(12) United States Patent  
Bowers (10) Patent No.: US 8,577,475 B2  
(45) Date of Patent: Nov. 5, 2013

(54) WIRELESS MONITORING APPARATUS USED IN CONJUNCTION WITH AN AUTOMATED EXTERNAL DEFIBRILLATOR (AED) SYSTEM FOR MULTIPLE PATIENT RESCUE DURING MASS CASUALTY INCIDENTS

(76) Inventor: Kyle R. Bowers, Boxborough, MA (US)

(*) Notice: Subject to any disclaimer, the term of this patent is extended or adjusted under 35 U.S.C. 154(b) by 575 days.

(21) Appl. No.: 12/722,216

(22) Filed: Mar. 11, 2010

(65) Prior Publication Data

US 2010/0234700 A1    Sep. 16, 2010

Related U.S. Application Data

(60) Provisional application No. 61/209,873, filed on Mar. 11, 2009.

(51) Int. Cl.
   *A61N 1/04*       (2006.01)
(52) U.S. Cl.
   USPC ..................................... 607/60; 607/5; 607/6
(58) Field of Classification Search
   USPC .............................................. 607/60, 60.5, 6
   See application file for complete search history.

(56) References Cited

U.S. PATENT DOCUMENTS

| | | | | |
|---|---|---|---|---|
| 5,275,572 A * | 1/1994 | Ungs et al. | ..................... | 434/265 |
| 6,708,050 B2 * | 3/2004 | Carim | ........................... | 600/372 |
| 7,289,761 B2 * | 10/2007 | Mazar | ................................ | 455/1 |
| 2006/0092029 A1 * | 5/2006 | Browne et al. | ............. | 340/573.1 |
| 2006/0136000 A1 * | 6/2006 | Bowers | ........................... | 607/5 |
| 2007/0032830 A1 * | 2/2007 | Bowers | ............................. | 607/5 |
| 2008/0009921 A1 * | 1/2008 | Mosesov et al. | ................ | 607/60 |
| 2008/0177341 A1 | 7/2008 | Bowers | | |

* cited by examiner

*Primary Examiner* — Christopher D Koharski  
*Assistant Examiner* — Michael Carey  
(74) *Attorney, Agent, or Firm* — Pandiscio & Pandiscio (57) ABSTRACT

A Wireless Monitoring Apparatus is used in conjunction with an automated external defibrillator (AED) system for patient rescue in mass-casualty incidents. The rescuer applies the device on each patient. The wireless monitoring apparatus automatically analyzes the patient's heart rhythm and communicates with the AED system. The AED system is therefore is able to display information with regard to each patient, notifies the rescuer on actions to take and can deliver defibrillation therapy if needed.

23 Claims, 9 Drawing Sheets

Method Of Monitor Communications With The AED

Method Of Monitor Data Flow To The AED

Methods Of Communications Link Protocol

FIG. 9A  FIG. 9B

WIRELESS MONITORING APPARATUS USED IN CONJUNCTION WITH AN AUTOMATED EXTERNAL DEFIBRILLATOR (AED) SYSTEM FOR MULTIPLE PATIENT RESCUE DURING MASS CASUALTY INCIDENTS

REFERENCE TO PENDING PRIOR PATENT APPLICATION

This patent application claims benefit of prior U.S. Provisional Patent Application Ser. No. 61/209,873, filed Mar. 11, 2009 by Kyle R. Bowers for WIRELESS MONITORING APPARATUS USED IN CONJUNCTION WITH AN AUTOMATED EXTERNAL DEFIBRILLATOR (AED) SYSTEM FOR MULTIPLE PATIENT RESCUE DURING MASS CASUALTY INCIDENTS, which patent application is hereby incorporated herein by reference.

FIELD OF THE INVENTION

This invention relates to Automated External Defibrillator (AED) Systems in general, and more particularly to a Wireless Monitoring Apparatus used in conjunction with an Automated External Defibrillator (AED) System for multiple patient rescue.

BACKGROUND OF THE INVENTION

In mass casualty incidents such as transportation, terrorist or military, rescuers must treat several patients at the same time, requiring several AEDs or a new system adapted to monitor several patient's vital signs at the same time and provide defibrillation therapy when necessary. Such a system that can monitor several patients at the same time allows a single rescuer to treat patients in a triage situation. Such an example is a military doctor or trained individual that must treat several soldiers after attack from an explosive device. Such an individual using a new system adapted to treat the critically wounded soldiers may be the difference between life and death in remote locations such as open battlefields where medical doctors and/or hospitals may be inaccessible. The system itself uses wireless communications to exchange information (via transceiver) with regard to the patient's vital signs and other relevant information. The rescuer applies the monitoring apparatus directly to the bare skin patient's chest. The apparatus then analyzes the patient's ECG for cardiac arrest, communicates the information to the AED and the AED alerts the rescuer that a soldier is in cardiac arrest and requires defibrillation therapy. The rescuer can then quickly provide therapy and continue monitor the other soldiers.

SUMMARY OF THE INVENTION

In the teaching of the Automated external defibrillator (AED) system with multiple patient wireless monitoring capability for use in mass casualty incidents, US Patent Application 20080177341, it becomes clear to the inventor that the wireless monitoring apparatus should have advanced features, as to make the system as a whole, lower-cost and more marketable. Allowing the monitoring apparatus to "off-load" the automated external defibrillator also reduces complexity, band-width requirements and allows an AED system which can monitor a greater number of patients without having to increase system peripherals and computer architecture.

In accordance with one preferred form of the present invention, the new wireless monitoring apparatus has circuitry and a controller to analyze the patient's ECG and other parameters by itself, eliminating the need to transmit the information in real-time to the AED for analysis. Thus, the current invention is not burdened with large amounts of data from many different sources, leading to operating systems complexities and problems well known by those skilled in the art.

In accordance with one preferred form of the present invention, the wireless monitoring apparatus contains a controller circuit which operates the device.

In accordance with one preferred form of the present invention, the controller circuit contains one or more microprocessors, microcontrollers, memory, and other circuitry to enable wireless monitoring apparatus operation.

In accordance with one preferred form of the present invention, the wireless monitoring apparatus contains circuitry to allow the apparatus to communicate wirelessly to an AED, a computer system, a wireless network or other wireless devices well known by those skilled in the art.

In accordance with one preferred form of the present invention, the wireless monitoring apparatus contains an analog-to-digital converter (A/D) and other analog or digital circuitry.

In accordance with one preferred form of the present invention, the wireless monitoring apparatus contains a battery and is self-powered. The battery contained within the apparatus may be removable, disposable, rechargeable, non-rechargeable, non-removable or any combination of the above well known by those skilled in the art. The apparatus also contains circuitry which allows measurement of the battery voltage and/or temperature. The apparatus is capable of storing this information in memory and may transmit this data other data with regard to the battery to the AED or wireless system described previously.

In accordance with one preferred form of the present invention, the wireless monitoring apparatus contains an impedance analysis circuit to determine if the wireless monitoring apparatus is applied to the patient. The impedance analysis circuit may also measure the trans-thoracic impedance of the patient storing the measurement in memory and/or transmitting the information to the AED or other wireless system described previously.

In accordance with one preferred form of the present invention, the wireless monitoring apparatus contains memory to store other information about the patient, such as the patient's ECG data. The wireless monitoring apparatus can transmit the ECG data and other relevant information to the AED in real-time upon request from the AED. This allows the rescuer to view the patient's ECG signal in real-time on the display of the AED. The rescuer may also decide to view a different wireless monitoring apparatus ECG based on the ECG of the current apparatus.

In accordance with another preferred form of the present invention, the wireless monitoring apparatus can transmit the ECG or other data stored in memory to a computer system upon request. The computer system runs a program which communicates with the wireless monitoring apparatus and may exchange, remove, download, upload or delete any form of data with the apparatus. The computer system may be an AED or other wireless system described previously.

In accordance with one preferred form of the present invention, the wireless monitoring apparatus is adapted to monitor patient parameters other than the patient's ECG or impedance, e.g., patient pulse and heart rate, patient temperature, patient blood pressure, patient blood oxygen level, etc. As those skilled in the art understand, the wireless monitoring apparatus may be adapted to communicate with any such wireless device that may provide information about the patient's health, care, identity or any other information about the patient.

In accordance with one preferred form of the present invention, the wireless monitoring apparatus contains a release liner, that when peeled away, activates the device and exposes the monitor electrodes. In accordance with another preferred form the present invention, the wireless monitoring apparatus release liner contains a component that causes activation of the device. As those skilled in the art can appreciate, the component may be an active or inactive device.

BRIEF DESCRIPTION OF THE DRAWINGS

These and other objects and features of the present invention will be more fully disclosed or rendered obvious by the following detailed description of the preferred embodiments of the present invention, which are to be considered together with the accompanying drawings wherein like numbers refer to like elements and further wherein.

DETAILED DESCRIPTION OF THE PREFERRED EMBODIMENTS

In accordance with the present invention, the new wireless monitoring apparatus is a stand-alone device, capable of determining if a patient requires therapy and alerting the rescuer of such condition. The wireless monitoring apparatus may also communicate and work in conjunction with an AED or other monitoring device. In addition, several wireless monitoring apparatuses may communicate and work in conjunction with an AED or other device to make a complete system to help a single rescuer treat several patients in a triage situation.

Figure 1:
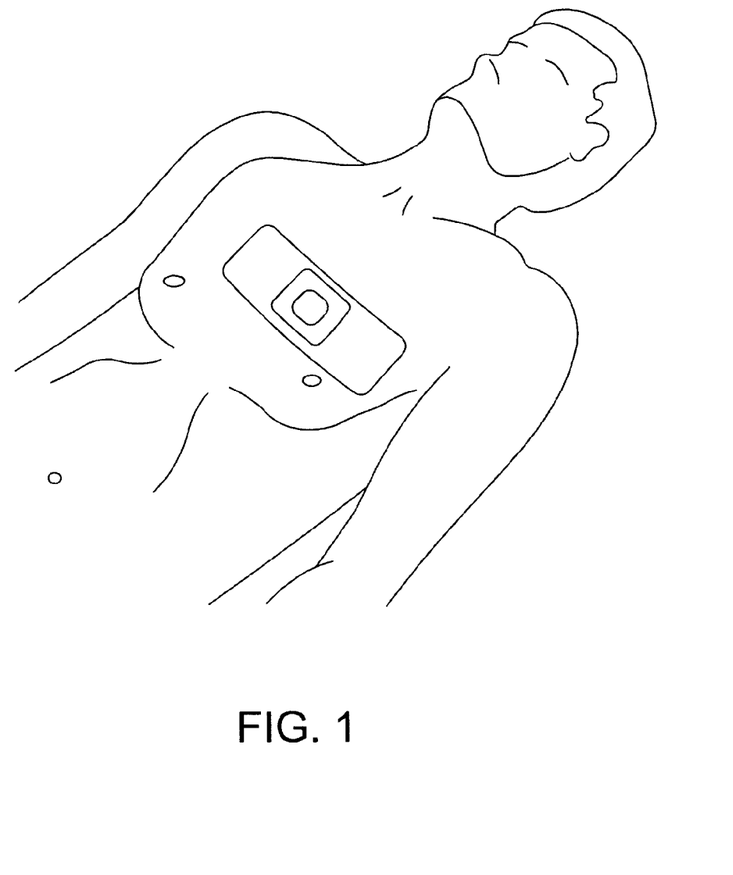
FIG. 1 is a pictorial of one concept the new wireless monitoring apparatus attached to the patient.
Figure 2:
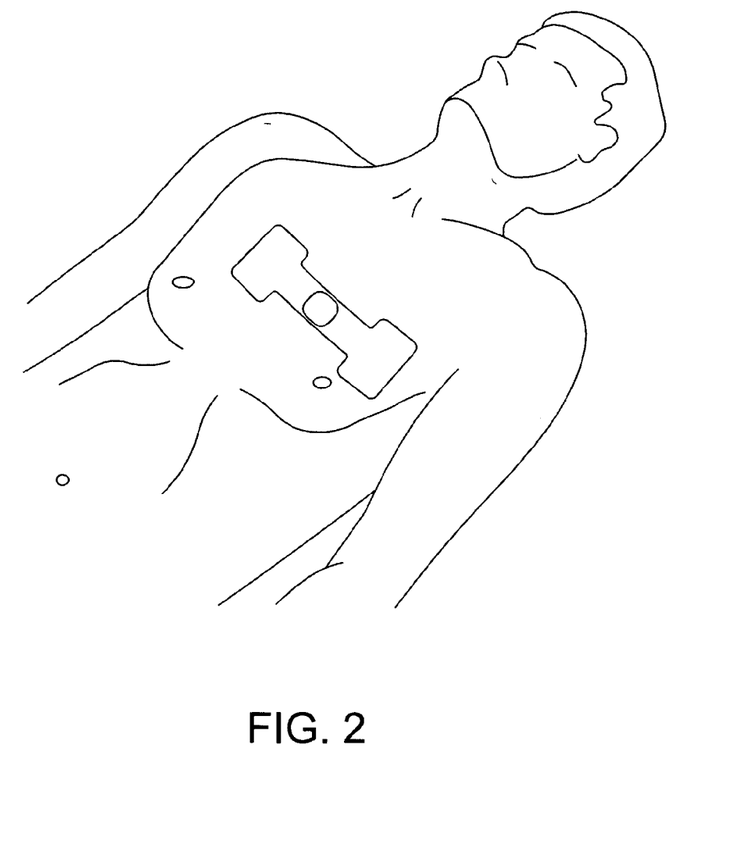
FIG. 2 is a pictorial of another concept the new wireless monitoring apparatus attached to the patient.
Figure 8:
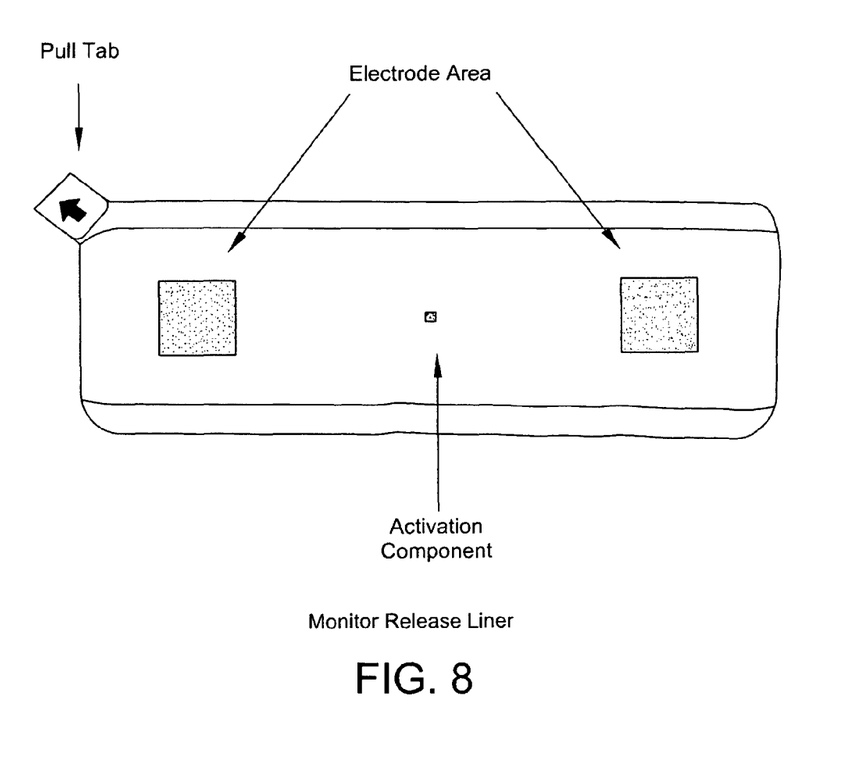
FIG. 8 is a pictorial of a concept the new wireless monitoring apparatus release liner detached.

FIGS. 1 and 2 show concepts of the wireless monitoring apparatus applied to the patient. The rescuer peels off a release liner (shown in FIG. 8) that exposes the electrodes. The electrode area shown in FIG. 8 is square, but the area may be round or any other shape. The release liner contains an "activation" component that causes the wireless monitoring apparatus to automatically power-on when the liner is removed. The activation component shown in FIG. 8 is a resistor. This allows an identification of the type of monitor being used. In other words, there may be non-clinical versions that are used for training and allow a resealing, so that the training monitor can be used multiple times. The wireless monitoring apparatus communicates this information and allows the system to be put in "training mode" for specific configurations of the AED. Other versions of the release liner may contain simply a wire or another component. The release liner contains instructions and diagrams that show the rescuer where to place the wireless monitoring apparatus, how to remove the liner, etc.

Although these instructions are provided, removal of the release liner is easy and intuitive; the user simply peels the pull tab shown in FIG. 8 to remove the liner. In addition, the wireless monitoring apparatus need not be located exactly as shown in the diagrams and will work in almost any position as long as it is located around the heart.

The electrodes and surrounding pad may contain a hydrogel, electrically conductive adhesive or other compound which serves to connect the wireless monitoring apparatus to the patient and helps to hold the device in place.

The wireless monitoring apparatus shown in FIGS. 1 and 2 is in Lead-I configuration, but could also be adapted for Lead-II, 3-Lead or other configurations as well.

Figure 3:
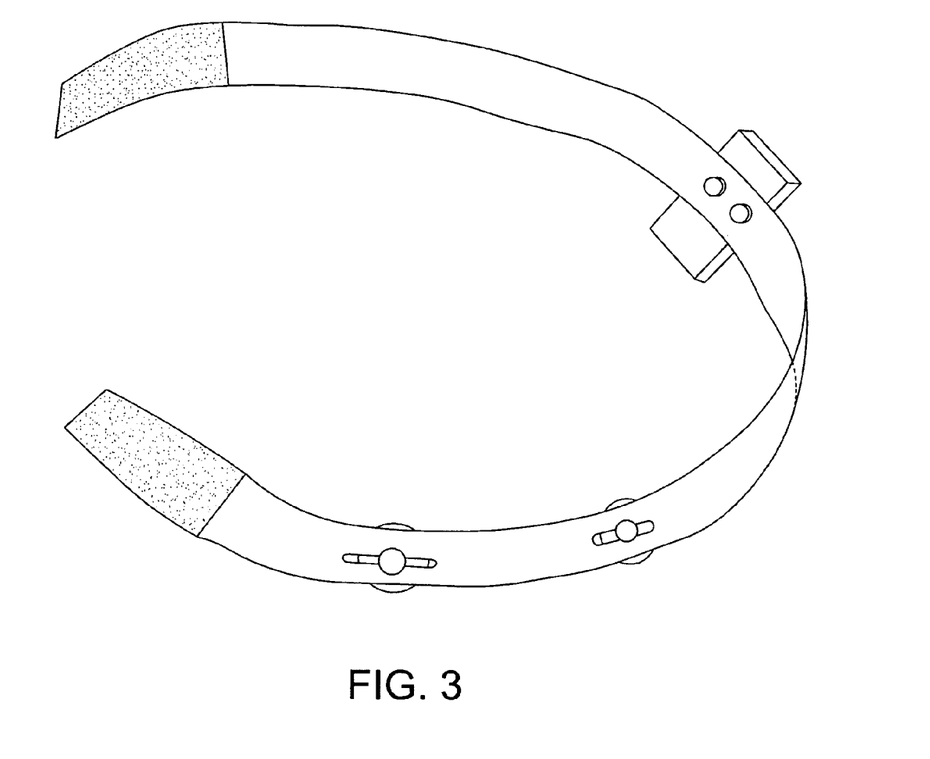
FIG. 3 is a pictorial of yet another concept the new wireless monitoring apparatus

Yet another concept of the wireless monitoring apparatus is shown in FIG. 3. This concept can be found in the inventor's previous teachings. However, the concepts shown in FIGS. 1 and 2 may contain features of the concept shown in FIG. 3. Such examples of these features are straps or other retaining methods, the use of inexpensive, off-the-shelf snap electrodes, movable electrodes, multiple electrodes, removable electronics, etc.

Figure 4:
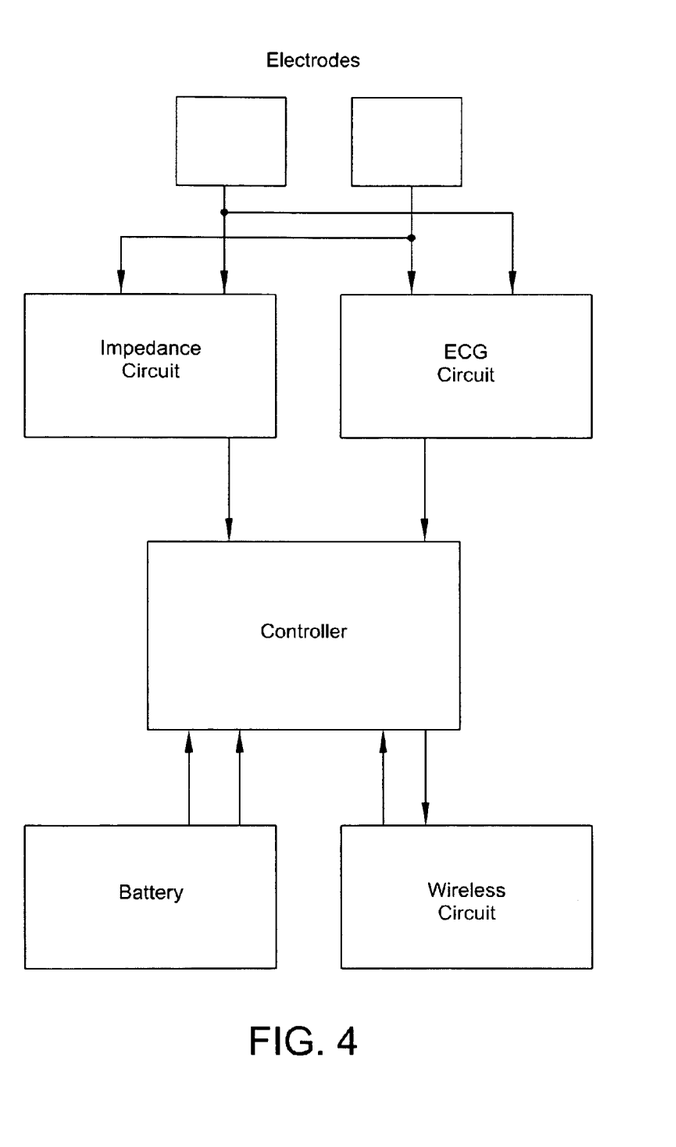
FIG. 4 is a block diagram showing a high-level system diagram of the new wireless monitoring apparatus.

A simple block diagram is shown in FIG. 4. The wireless monitoring apparatus can be broken down into six basic blocks shown in the diagram.

Figure 5:
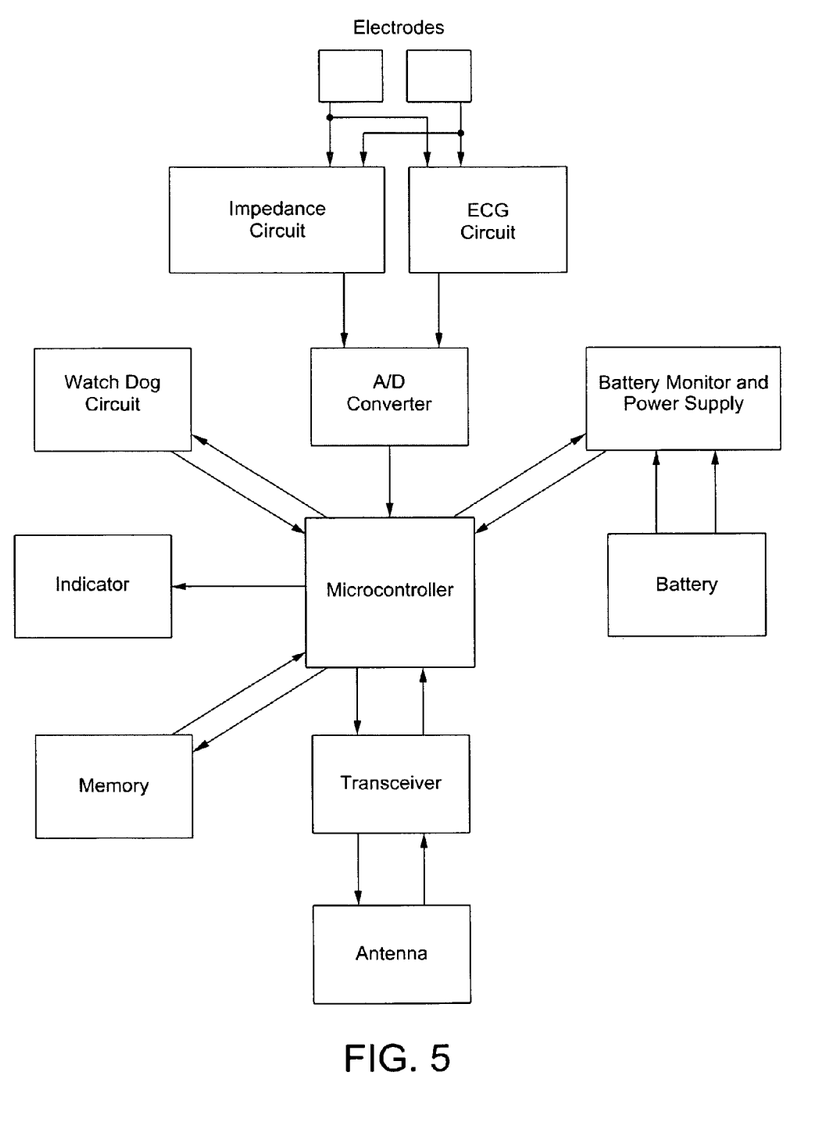
FIG. 5 is a block diagram showing more detailed system diagram of the new wireless monitoring apparatus system.

A more detailed block diagram of the new wireless monitoring apparatus is shown in FIG. 5. The controller circuit contains the necessary components and circuits to assure the wireless monitoring apparatus works efficiently and reliably. Such examples of these are a watch-dog circuit which causes the indication system to warn the rescuer of a malfunction of the controller or other circuits. In accordance with the present invention, the watch-dog circuit and status indication system are configured so that if either fail, the status indication system indicates that the device is unusable, ensuring the entire system is failsafe.

In accordance with the present invention, the wireless monitoring apparatus runs a periodic self-test and uses the status indication system to notify the user of the results. The periodic self-test checks the wireless monitoring apparatus circuitry, controllers, batteries, etc.

The indication system contains visual and audible components to alert the user of a number of conditions. Examples of such conditions are alerting the rescuer that the patient requires therapy or attention, locating the patient if indicated by an AED or other monitoring device, alerting the user of low battery, other conditions within the device, etc.

Figure 9A:
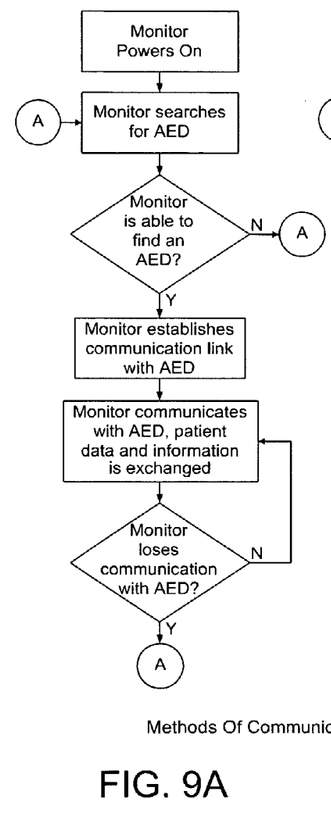
FIGS. 9A and 9B are flow diagrams showing example methods of the wireless monitoring apparatus communication link protocol.
Figure 9B:
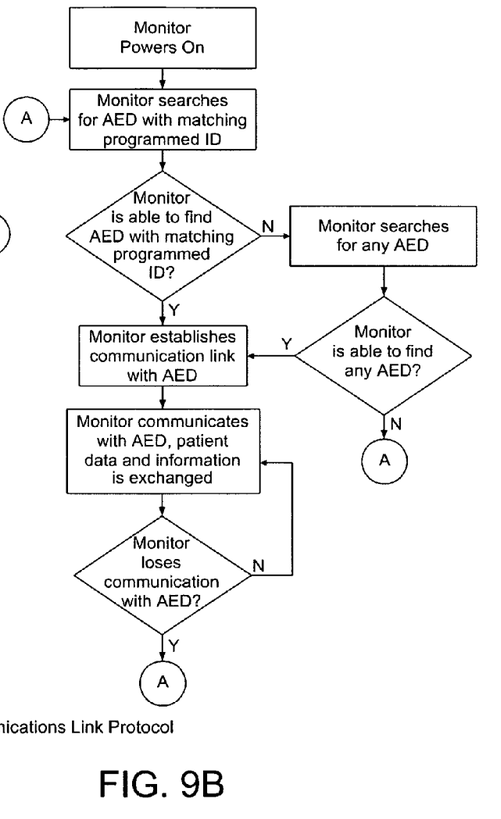

In accordance with the present invention, the new wireless monitoring apparatus uses a proprietary method to communicate with an AED or other type of monitoring device. As described previously, the wireless monitoring apparatus powers-on when the release liner is removed, it then begins to "search" for an AED using a communication link protocol. In accordance with the present invention, the new wireless monitoring apparatus uses programmable parameters to determine how the communication link is established. In FIG. 9A, the simplest protocol is used to establish a link between the wireless monitoring apparatus and an AED. In FIG. 9B, the protocol adds a unique ID which is pre-programmed into the wireless monitoring apparatus before it is placed into service. There is therefore a match between the AED and the wireless monitoring apparatuses which are placed in service with the AED; most likely in the same carrying case of the AED, so that the rescuer need not be concerned with the wireless monitoring apparatus connecting to other AEDs placed in service. This simplifies the process in the event of a large triage situation where there are several groups of rescuers treating specific groups of patients. In accordance with the present invention, the new wireless monitoring apparatus uses other pre-programmed parameters and can easily be adapted to use newer technologies. As those skilled in the art can appreciate, examples of these are using GPS to locate the nearest AED, using the AED connected to chose the monitoring device to establish a new link with, using the AED to disconnect with the wireless monitoring apparatus, etc. and any combination thereof. As those skilled in the art understand, the above decision tree blocks could easily be added to the flow diagrams in FIGS. 9A and 9B. In addition, as those skilled in the art can appreciate and in accordance with the present invention, the new wireless monitoring apparatus affords the ability to first be used with an AED in any form or another device as described above and then be used with a subsequent monitoring device. As those skilled in the art can appreciate, examples of such subsequent devices are, but not limited to, other manufacturer's AEDs, defibrillators, patient monitors, etc. In accordance with the present invention, the new wireless monitoring apparatus will work with any other device that is adapted to follow the methods described in the present invention. In current device technologies, USB dongles, sticks, PCMCIA, WiFi cards, etc. make adapting other manufacturer's devices to work in conjunction with the new wireless monitoring apparatus a reality. This allows continuation of health care possible throughout the complete chain of rescue; from the initial triage situation, to the transport of the patient to the hospital and transport within the hospital to the emergency care units.

Figure 6:
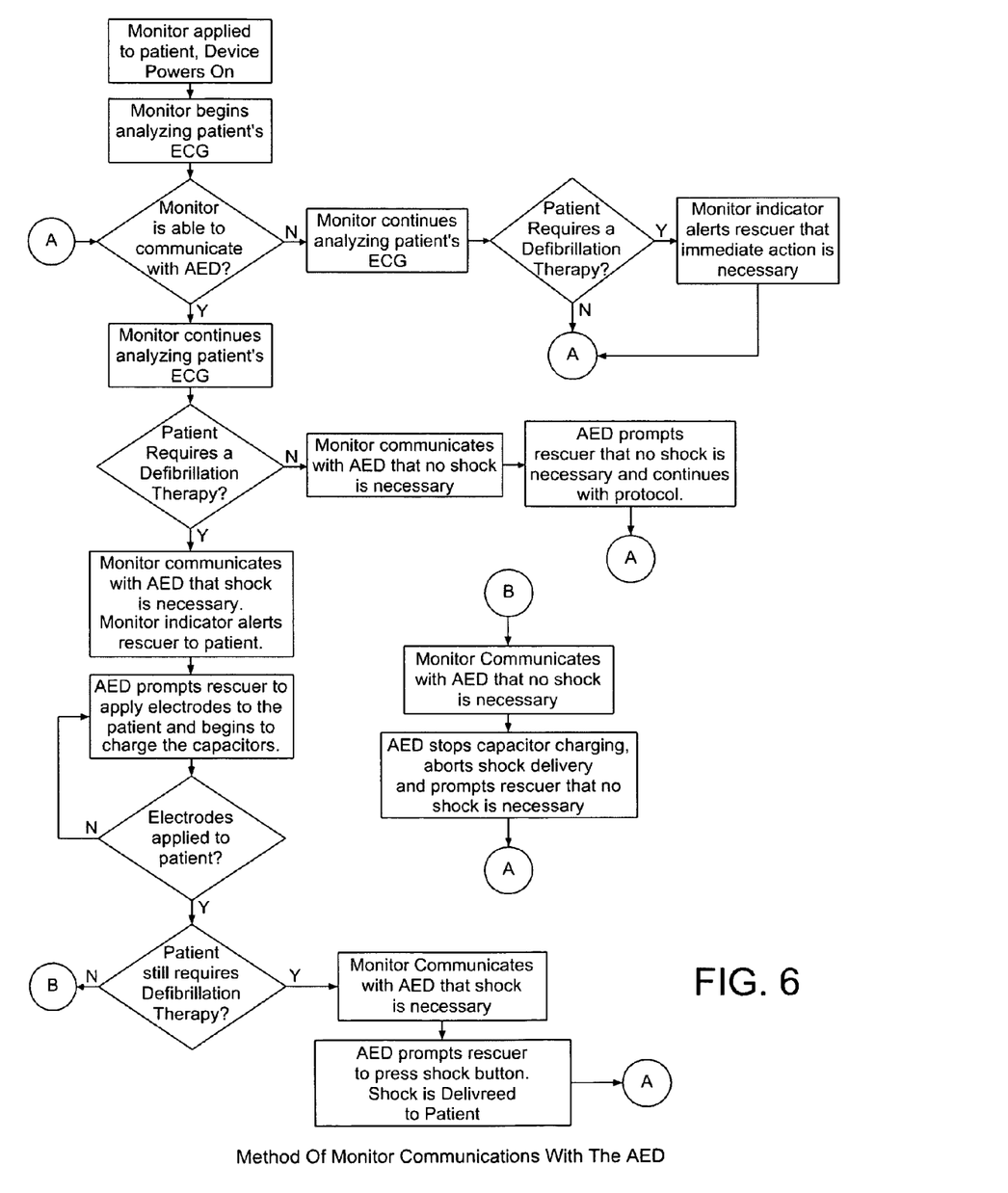
FIG. 6 is a flow diagram showing an example method of the wireless monitoring apparatus communications with the AED.

FIG. 6 shows an example of the method of the wireless monitoring apparatus communications with an AED. In accordance with the present invention, the wireless monitoring apparatus immediately begins analyzing the patients ECG and other parameters. As described above, the wireless monitoring apparatus begins to "search" for an AED using a predetermined protocol. As shown in FIG. 6, if the wireless monitoring apparatus can not communicate with an AED or other wireless monitoring device for whatever reason, it can still operate in stand-alone mode and indicate to the trained user the condition of the patient and what actions or therapies are required. In accordance with the present invention, the wireless monitoring apparatus indication system uses beeps of different tones, durations, frequency or any combination thereof. In addition, these beeps may be used in combination of one or more flashing indicator lights.

If the wireless monitoring apparatus finds an AED, it begins to send the AED information about the patient. If the patient does not require defibrillation therapy, it communicates this to the AED, which prompts the rescuer and then continues with the protocol according to AHA (American Heart Association) and/or ERC (European Resuscitation Council) guidelines. If the patient does require defibrillation therapy, then the wireless monitoring apparatus communicates that a shock is required and the AED begins to charge the capacitors and prepares to deliver a shock. The wireless monitoring apparatus indicates the patient for the rescuer to apply the defibrillation electrodes and by the time the electrodes are applied, the AED is ready to deliver a defibrillation shock. As those skilled in the art can appreciate, the timeline from application of the wireless monitoring apparatus to the time therapy is delivered is expedited, as taught by the present invention.

Figure 7:
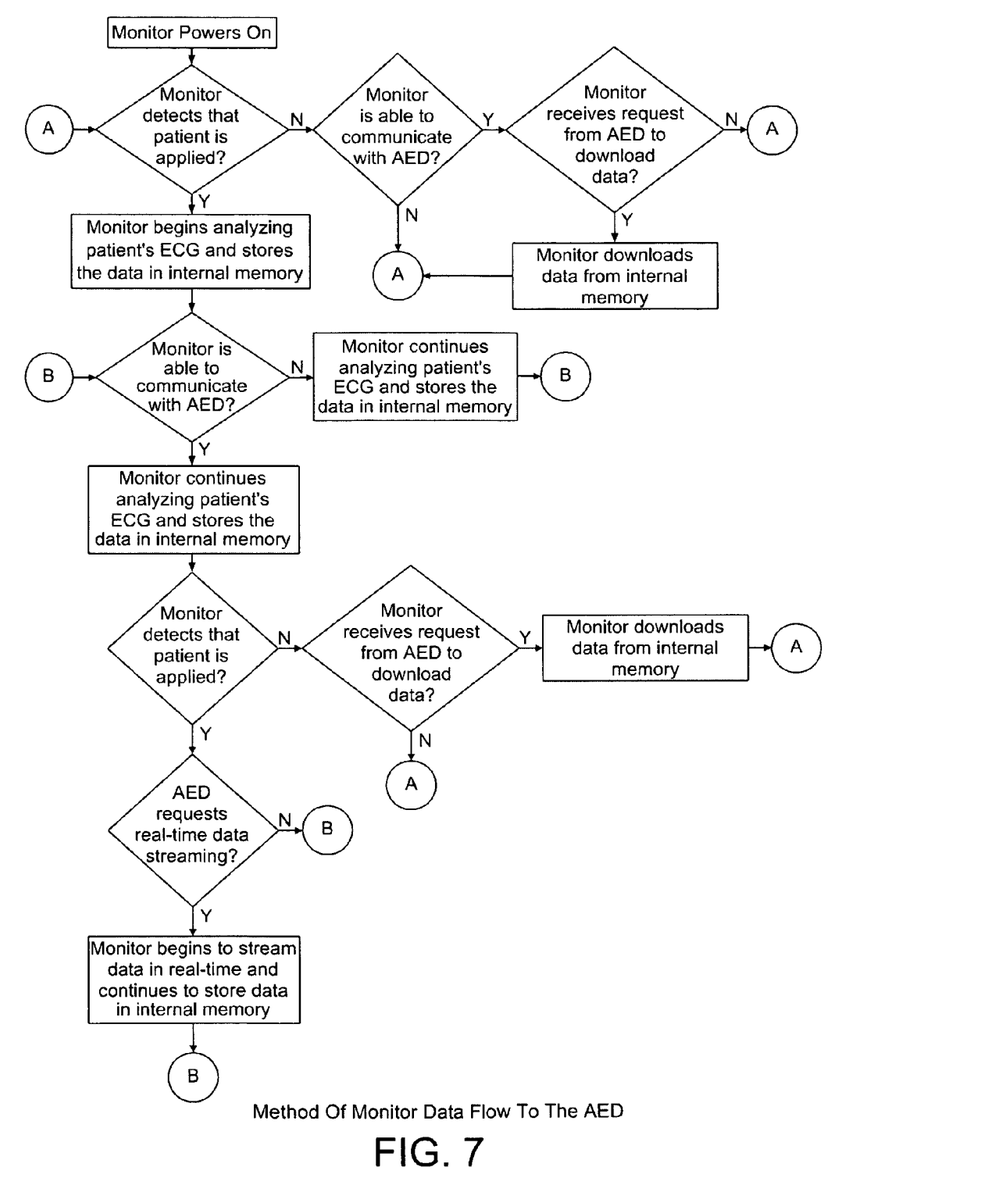
FIG. 7 is a flow diagram showing an example data flow communications to the AED.

In accordance with the present invention and described above, the wireless monitoring apparatus has many modes of operation. It has become clear to the inventor that it is advantageous for the wireless monitoring apparatus to analyze the patient's ECG and other parameters itself, thereby removing the burden of transmitting the data to the AED, for the AED to analyze and then determine actions. However, in accordance with the present invention, there are modes in which the wireless monitoring apparatus does send the ECG data in real-time to the AED. Such mode of operation is when the rescuer selects the patient's ECG to view, using a menu on the AED. The rescuer can then view the patient's ECG in real-time on the AED's screen and determine what actions, if any are necessary. In FIG. 7 an example method of the wireless monitoring apparatus data flow to the AED is shown. The reader should distinguish that there are two types of data flow; (1) The data is sent in real-time or "streaming" so that the rescuer can view the data on the AED screen and (2) The data is read from internal memory and is downloaded to the AED. As those skilled in the art can appreciate, the downloading of data may be to an AED, computer or other device. As those skilled in the art understand and shown in FIG. 7, the wireless monitoring apparatus only chooses to download the data from internal memory during non-clinical periods or after a clinical event has elapsed.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A system for patient rescue, the system comprising:
a defibrillator comprising:
   a capacitor;
   a battery for selectively charging the capacitor;
   a first electrode selectively connected to the capacitor for delivering a shock to a patient;
   defibrillator control circuitry for selectively causing (a) the battery to charge the capacitor, and (b) the capacitor to discharge through the first electrode; and
   a first wireless communications unit connected to the defibrillator control circuitry; and
a stand-alone wireless monitor comprising:
   a second electrode for attachment to a patient;
   a release liner releasably secured to the second electrode;
   monitor control circuitry connected to the release liner and to the second electrode; and
   a second wireless communications unit connected to the monitor control circuitry;
the monitor control circuitry being configured so that when the release liner is removed from the second electrode and the second electrode is positioned on a patient, the monitor control circuitry reads the second electrode, determines whether the patient is experiencing a shockable event and, if the patient is experiencing a shockable event, wirelessly instructs the defibrillator control circuitry to charge the capacitor.

2. A system according to claim 1 wherein the monitor control circuitry measures and analyzes the patient's ECG signal.

3. A system according to claim 2 wherein the monitor control circuitry measures and analyzes the patient's transthoracic impedance signal.

4. A system according to claim 3 wherein the monitor control circuitry further measures and analyzes at least one from the group consisting of:
patient temperature;
patient blood oxygen level; and
patient blood pressure.

5. A system according to claim 2 wherein the monitor control circuitry analyzes the patient's ECG to determine if the patient's heart rhythm is shockable.

6. A system according to claim 5 wherein the monitor control circuitry determines if the patient's heart rhythm is shockable and communicates the results to an AED.

7. A system according to claim 5 wherein the monitor control circuitry determines if the patient's heart rhythm is shockable and uses a status indication system to notify the rescuer of the results.

8. A system according to claim 5 wherein the monitor control circuitry measures and stores patient data in internal memory.

9. A system according to claim 5 wherein the monitor control circuitry transmits patient data in real-time to another device.

10. A system according to claim 8 wherein the monitor control circuitry transmits patient data stored in internal memory to another wireless device.

11. A system according to claim 10 wherein the monitor control circuitry transmits patient data stored in internal memory only during non-clinical periods.

12. A system according to claim 11 wherein the monitor control circuitry has a unique ID number which is transmitted to another device.

13. A system according to claim 1 wherein the monitor control circuitry comprises an indication system having visual and audible components to alert a rescuer of a number of conditions.

14. A system according to claim 13 wherein the monitor control circuitry runs a periodic self-test and uses the status indication system to notify a user of the results.

15. A system according to claim 14 wherein the monitor control circuitry contains a watch-dog circuit that works in conjunction with the status indication system, so that if any circuit mal-functions, the status indication system notifies the user in a failsafe manner.

16. A system according to claim 15 wherein the monitor control circuitry uses a communication link protocol to connect with an AED or other wireless device.

17. A system according to claim 16 wherein the communication link protocol uses a pre-programmed parameter to decide which device it connects with.

18. A system according to claim 16 wherein the communication link protocol uses GPS location to decide which device it connects with.

19. A system according to claim 16 wherein, upon request from a wireless device, the apparatus establishes a communications link.

20. A system according to claim 16 wherein upon request, the monitor control circuitry changes its communications link with the current device to a new device.

21. A system according to claim 1 wherein the monitor release liner contains a component that indicates that the device is for training use or clinical use.

22. A system according to claim 1 wherein the release liner component is sensed by the monitor control circuitry and this information is communicated to an AED or other device to place it in training or clinical modes.

23. A system according to claim 1 wherein the electronics are removable.

* * * * *